United States Patent
Owaki et al.

(10) Patent No.: US 11,932,201 B2
(45) Date of Patent: Mar. 19, 2024

(54) BIOMETRIC INFORMATION AUTHENTICATING DEVICE, AND BIOMETRIC INFORMATION AUTHENTICATING SYSTEM

(71) Applicants: KABUSHIKI KAISHA TOKAI RIKA DENKI SEISAKUSHO, Aichi (JP); TOYOTA JIDOSHA KABUSHIKI KAISHA, Aichi-ken (JP)

(72) Inventors: Rijin Owaki, Aichi (JP); Yosuke Ohashi, Aichi (JP); Takahiko Ando, Aichi (JP); Yuya Goto, Aichi-ken (JP); Yasuhisa Ohta, Aichi-ken (JP); Naoyuki Takada, Aichi-ken (JP); Daisuke Ogawa, Aichi (JP)

(73) Assignees: KABUSHIKI KAISHA TOKAI RIKA DENKI SEISAKUSHO, Aichi (JP); TOYOTA JIDOSHA KABUSHIKI KAISHA, Aichi-Ken (JP)

( * ) Notice: Subject to any disclaimer, the term of this patent is extended or adjusted under 35 U.S.C. 154(b) by 534 days.

(21) Appl. No.: 17/262,610

(22) PCT Filed: Aug. 1, 2019

(86) PCT No.: PCT/JP2019/030297
§ 371 (c)(1),
(2) Date: Jan. 22, 2021

(87) PCT Pub. No.: WO2020/027284
PCT Pub. Date: Feb. 6, 2020

(65) Prior Publication Data
US 2021/0261095 A1  Aug. 26, 2021

(30) Foreign Application Priority Data

Aug. 3, 2018 (JP) ................ 2018-146854

(51) Int. Cl.
*B60R 25/25* (2013.01)
*B60Q 3/292* (2017.01)
(Continued)

(52) U.S. Cl.
CPC ............ *B60R 25/252* (2013.01); *B60Q 3/292* (2017.02); *B60R 25/04* (2013.01); *G06V 10/141* (2022.01);
(Continued)

(58) Field of Classification Search
CPC ....... B60R 25/252; B60R 25/04; B60Q 3/292; G06V 10/141; G06V 40/10;
(Continued)

(56) References Cited

U.S. PATENT DOCUMENTS 9,002,586 B2 * 4/2015 Feit ............... B60R 25/252
  701/1
2008/0187190 A1  8/2008 Shin et al.
(Continued)

FOREIGN PATENT DOCUMENTS

EP    3848258 A1   7/2021
JP    2002-269512 A   9/2002
(Continued)

*Primary Examiner* — Alan D Hutchinson
(74) *Attorney, Agent, or Firm* — Thomas W. Cole; Calderon Safran & Cole P.C.

(57) ABSTRACT

A biometric information authenticating device includes a biometric information sensor to detect contact of an operating finger with a reading surface and to read biometric information of the operating finger, an illumination unit including at least one light source, and a control unit to indicate completion of reading of the biometric information by an illumination pattern including a combination of turning on and off of the at least one light source.

10 Claims, 5 Drawing Sheets

(51) Int. Cl.
*B60R 25/04* (2013.01)
*G06V 10/141* (2022.01)
*G06V 40/10* (2022.01)
*G06V 40/12* (2022.01)
*G06V 40/13* (2022.01)
*G06V 40/14* (2022.01)
*G06V 40/70* (2022.01)

(52) U.S. Cl.
CPC .......... *G06V 40/10* (2022.01); *G06V 40/1318* (2022.01); *G06V 40/1376* (2022.01); *G06V 40/70* (2022.01); *G06V 40/14* (2022.01)

(58) Field of Classification Search
CPC ........... G06V 40/1318; G06V 40/1376; G06V 40/70; G06V 40/14; A61B 5/0062; A61B 5/1172; G06F 21/32
See application file for complete search history.

(56) References Cited

U.S. PATENT DOCUMENTS

| | | | |
|---|---|---|---|
| 2014/0156149 A1 | 6/2014 | Feit | |
| 2018/0234415 A1* | 8/2018 | Fukuda | ................... G06F 21/32 |

FOREIGN PATENT DOCUMENTS

| | | |
|---|---|---|
| JP | 2003-037708 A | 2/2003 |
| JP | 2004-190380 A | 7/2004 |
| JP | 2008-062690 A | 3/2008 |
| JP | 2008-174095 A | 7/2008 |
| JP | 2017071316 A | 4/2017 |
| WO | 2017026446 A1 | 2/2017 |

* cited by examiner

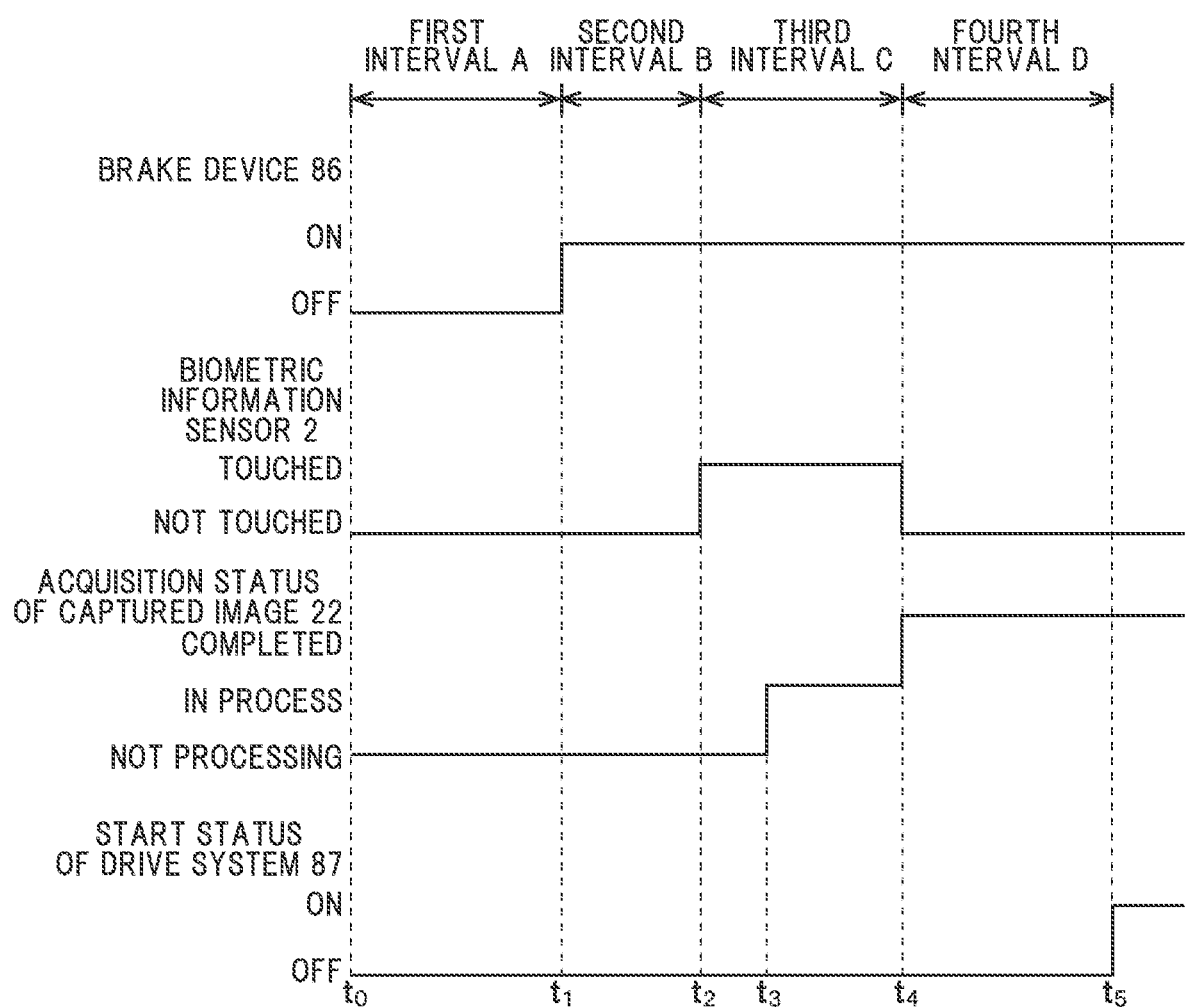

| | FIRST INTERVAL A | SECOND INTERVAL B | THIRD INTERVAL C | FOURTH INTERVAL D-1 | FOURTH INTERVAL D-2 |
|---|---|---|---|---|---|
| ILLUMINATION PATTERN a<br>SAME COLOR, SWITCHING BETWEEN BLINKING AND SOLID LIGHT | SLOW BLINKING WHITE LIGHT | RAPID BLINKING WHITE LIGHT | RAPID BLINKING WHITE LIGHT ⇩ | SOLID WHITE LIGHT | SOLID WHITE LIGHT ⇩ |
| ILLUMINATION PATTERN b<br>SOLID LIGHT ONLY, SWITCHING COLORS | SOLID WHITE LIGHT | SOLID WHITE LIGHT | SOLID WHITE LIGHT | SOLID BLUE LIGHT | SOLID BLUE LIGHT ⇩ |
| ILLUMINATION PATTERN c<br>SOLID LIGHT ONLY, SWITCHING COLORS | SOLID WHITE LIGHT | SOLID WHITE LIGHT ⇩ | SOLID WHITE LIGHT | SOLID BLUE LIGHT | SOLID RED LIGHT |
| ILLUMINATION PATTERN d<br>SOLID LIGHT ONLY, SWITCHING COLORS | SOLID WHITE LIGHT | SOLID WHITE LIGHT ⇩ | SOLID BLUE LIGHT | SOLID GREEN LIGHT | SOLID RED LIGHT |
| ILLUMINATION PATTERN e<br>SWITCHING BETWEEN BLINKING AND SOLID LIGHT, AND SWITCHING COLORS | SLOW BLINKING WHITE LIGHT<br>ENGINE START STOP | RAPID BLINKING WHITE LIGHT | SOLID BLUE LIGHT | SOLID GREEN LIGHT | SOLID RED LIGHT |

BIOMETRIC INFORMATION AUTHENTICATING DEVICE, AND BIOMETRIC INFORMATION AUTHENTICATING SYSTEM

CROSS-REFERENCE TO RELATED APPLICATIONS

The present application is a U.S. National Phase of PCT/JP2019/030297 filed on Aug. 1, 2019 claiming priority to Japanese Patent Application No. 2018-146854 filed on Aug. 3, 2018. The disclosure of the PCT Application is hereby incorporated by reference into the present Application.

TECHNICAL FIELD

The present invention relates to a biometric information authenticating device and a biometric information authenticating system.

BACKGROUND ART

A start control device is known which is provided with a start switch giving an instruction to start or stop a drive source, a start-up means for starting the drive source, a fingerprint sensor for reading fingerprints, and a control means which, based on inputs from the fingerprint sensor and the start switch, implements a start-up process to control activation of the start-up means (see, e.g., Patent Literature 1).

When the start switch gives an instruction to start, the control means of the start control device performs fingerprint verification by comparing a fingerprint read by the fingerprint sensor with a pre-registered fingerprint before start-up by the start-up means, and once a match is found, the control means authenticates the user as a genuine user and allows the start-up means to start up.

CITATION LIST

Patent Literature

Patent Literature 1: JP 2008/174095 A

SUMMARY OF INVENTION

Technical Problem

When a push operation is performed on the start switch, the start control device disclosed in Patent Literature 1 performs fingerprint verification and then starts the drive source in case that the result is a match. However, when such a start control device is configured to be, e.g., operated by a touch operation and verify a fingerprint, etc., timing to take the finger off is not clear without feedback about completion of fingerprint verification. Thus, users may not be able to take the finger off until the drive source is started, causing a problem of high operational burden.

It is an object of the invention to provide a biometric information authenticating device and a biometric information authenticating system which can reduce operational burden of users.

Solution to Problem

According to an embodiment of the invention, a biometric information authenticating device comprises:

a biometric information sensor to detect contact of an operating finger with a reading surface and to read biometric information of the operating finger;
an illumination unit comprising at least one light source; and
a control unit to indicate completion of reading of the biometric information by an illumination pattern including a combination of turning on and off of the at least one light source.

According to another embodiment of the invention, a biometric information authenticating system comprises:

a start switch device comprising a biometric information sensor to detect contact of an operating finger with a reading surface and to read biometric information of the operating finger, an illumination unit comprising at least one light source, and a control unit to control the illumination unit by an illumination pattern including a combination of turning on and off of the at least one light source; and
a vehicle control unit electromagnetically connected to the start switch device and each unit of a vehicle,
wherein the vehicle control unit determines the state of the vehicle and outputs vehicle information to the control unit based on a detection result of contact of the operating finger with the reading surface, status of reading of the biometric information, operation status of the vehicle, and start status of a drive system, and the control unit controls the illumination unit to produce the illumination pattern corresponding to the vehicle information.

Advantageous Effects of Invention

According to embodiments of the invention, it is possible to provide a biometric information authenticating device and a biometric information authenticating system which can reduce operational burden of users.

BRIEF DESCRIPTION OF DRAWINGS

FIG. 3 is a timing diagram of the start switch device in the embodiment.
FIG. 4 is an explanatory diagram illustrating illumination patterns of the start switch device in the embodiment.

DESCRIPTION OF EMBODIMENTS

Summary of the Embodiment

A biometric information authenticating device in the embodiment has a biometric information sensor to detect contact of an operating finger with a reading surface and to read biometric information of the operating finger, an illumination unit having at least one light source, and a control unit to indicate completion of reading of the biometric information by an illumination pattern including a combination of turning on and off of the at least one light source.

With this biometric information authenticating device, users can know completion of biometric information reading since illumination is provided. Therefore, timing to take the finger off is clear and it is thus possible to reduce operational burden of users, as compared to when illumination is not provided.

EMBODIMENT (General Configuration of a Start Switch Device 1)

Figure 1A:
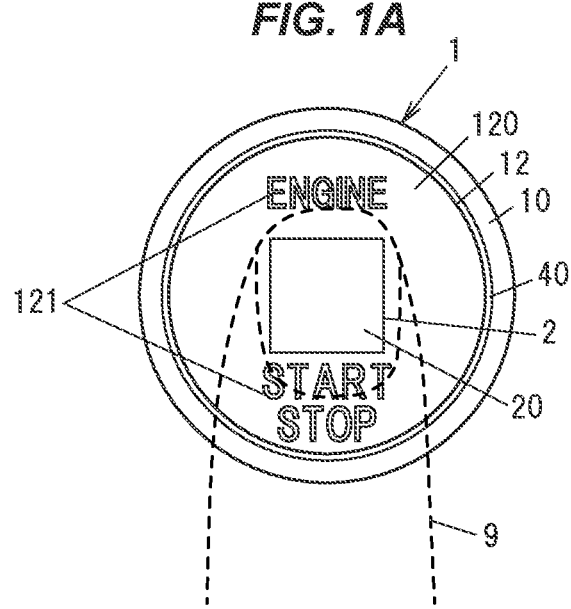
FIG. 1A is a front view showing a start switch device in an embodiment.
Figure 1B:
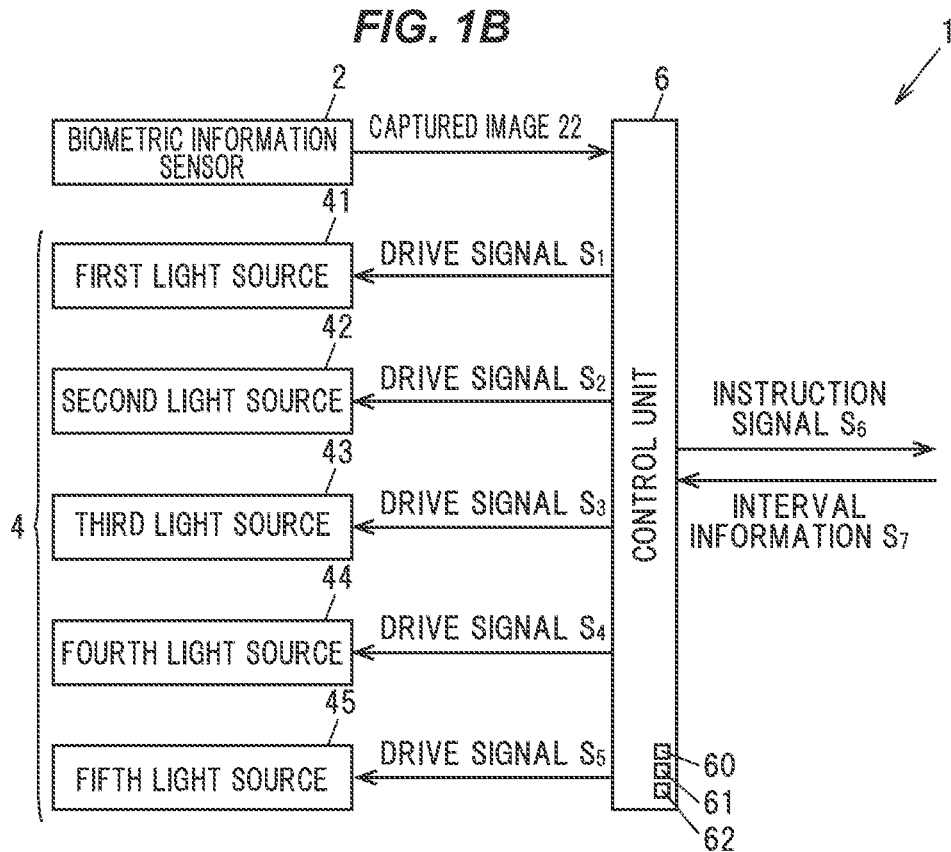
FIG. 1B is a block diagram illustrating the start switch device in the embodiment.
Figure 2A:
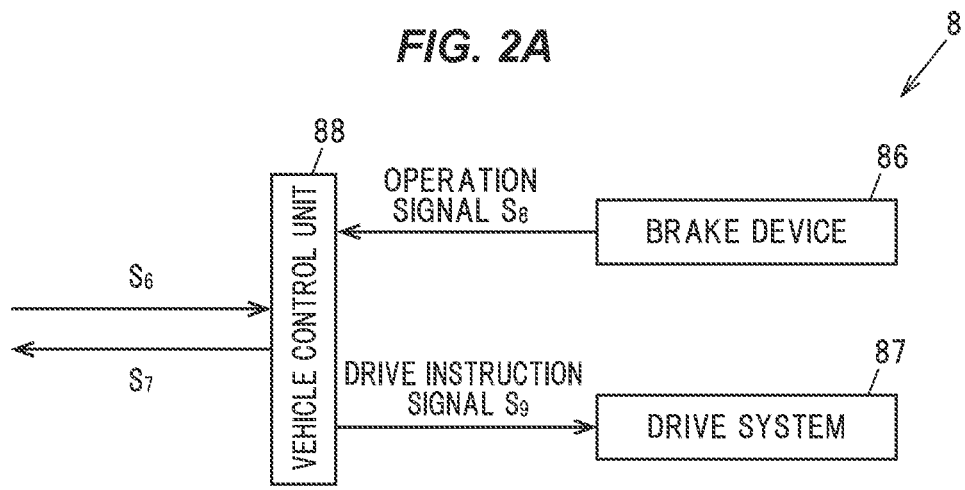
FIG. 2A is a block diagram illustrating a vehicle in which the start switch device in the embodiment is mounted.
Figure 2B:
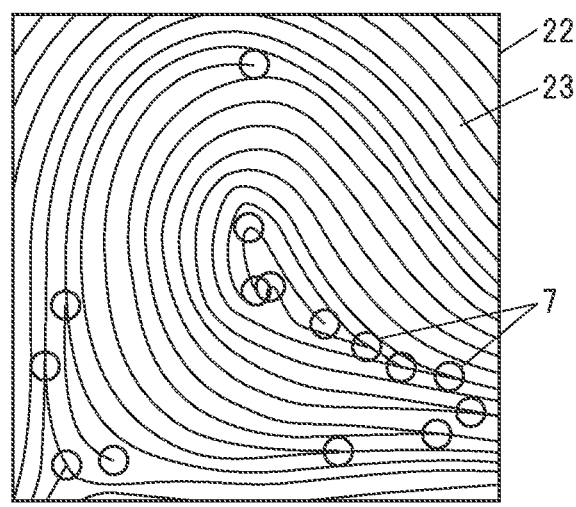
FIG. 2B is an explanatory diagram illustrating a captured image which is captured by a biometric information sensor of the start switch device in the embodiment.

FIG. 1A is a front view showing a start switch device in the embodiment and FIG. 1B is a block diagram illustrating the start switch device. FIG. 2A is a block diagram illustrating a vehicle in which the start switch device in the embodiment is mounted and FIG. 2B is an explanatory diagram illustrating a captured image which is captured by a biometric information sensor. FIG. 3 is a timing diagram of the start switch device in the embodiment. FIG. 4 is an explanatory diagram illustrating examples of illumination patterns of the start switch device in the embodiment.

In each drawing of the embodiment described below, a scale ratio may be different from an actual ratio. In addition, in FIGS. 1B and 2A, flows of main signals and information are indicated by arrows.

The start switch device 1 as the biometric information authenticating device is arranged on, e.g., a panel in front of an operator sitting in a driver's seat, a floor console located between the driver's seat and the front passenger seat, or a steering wheel, etc. This start switch device 1 can instruct a vehicle control unit 88 of a vehicle 8 to start, or to prepare to start, a drive system 87 of the vehicle 8 by a touch operation (ON operation), and instruct to stop the drive system 87 by a next touch operation (OFF operation).

Start-up of the drive system 87 of the vehicle 8 and power state transition of the vehicle 8 are judged by, e.g., the vehicle control unit 88 based on an instruction signal $S_6$ output from the start switch device 1 and the operating conditions for a brake device 86, etc., of the vehicle 8. The result of judgment is output as, e.g., interval information $S_7$ shown in FIGS. 1B and 2A to the start switch device 1.

In particular, when the drive system 87 is an internal combustion engine (an engine), the engine is started by a touch operation performed in a state in which the operating conditions for a shifting device or the braking device 86 are met. Meanwhile, when the drive system 87 is a motor, preparation for start, which is a current supply to the motor, is carried out by a touch operation performed in a state in which the above-described operating conditions are met. Furthermore, when the drive system 87 is an engine/motor hybrid, start or preparation for start corresponding to the drive system 87 prioritized at the time of start is carried out by a touch operation performed in a state in which the above-described operating conditions are met. An OFF operation performed after this ON operation gives an instruction to stop the drive system 87.

Then, when a touch operation is performed without activation of the brake device 86 which is the operating condition, the start switch device 1 outputs the instruction signal $S_6$ to perform transition of power state such as between OFF (power off), ACC (allowing some of electronic devices to be used) or ON (allowing all electronic devices to be used), as an example. The vehicle control unit 88 controls the power source based on, e.g., such an instruction signal $S_6$ and the above-mentioned operating condition. In this regard, the biometric information authenticating device is not limited to the start switch device 1 and may be used for, e.g., authentication for locking or unlocking doors or authentication for logging in to electronic devices, etc.

The start switch device 1 has, e.g., a biometric information sensor 2 that detects contact of an operating finger 9 with a reading surface 20 and reads biometric information 23 of the operating finger 9, an illumination unit 4 having at least one light source, and a control unit 6 that indicates completion of reading of the biometric information 23 by means of an illumination pattern produced by a combination of turning on and off of the at least one light source, as shown in FIGS. 1A and 1B.

When contact of the operating finger 9 with the reading surface 20 is detected, the control unit 6 controls the illumination unit 4 to produce a different illumination pattern from the illumination pattern produced at the time of completion of reading of the biometric information 23.

In addition, the control unit 6 controls the illumination unit 4 to change the illumination pattern when reading of the biometric information 23 is successful and when failed.

Upon successful authentication of the biometric information 23 that is read during contact of the operating finger 9, the control unit 6 outputs a signal to permit the drive system 87 of the vehicle 8 to start. This signal is, e.g., the instruction signal $S_6$.

The reading surface 20 of the biometric information sensor 2 is arranged so to be able to read the biometric information 23 of the operating finger 9 in contact with an operation surface 120 of an operating portion 12. Then, the illumination unit 4 is configured to output light encircling the operation surface 120.

The start switch device 1 has, e.g., a cylindrical main body 10 as shown in FIG. 1A, and a bottom surface (the operation surface 120) of the main body 10 is the operating portion 12. The operation surface 120 of the operating portion 12 has, e.g., a circular shape and is configured that the rectangular reading surface 20 is exposed at the center.

As an example, the vehicle 8 is provided with the brake device 86, the drive system 87 and the vehicle control unit 88, as shown in FIG. 2A.

The brake device 86 is configured to output, e.g., an operation signal $S_8$, which indicates that it is being operated, to the vehicle control unit 88. Then, the drive system 87 starts, etc., based on, e.g., a drive instruction signal $S_9$ output from the vehicle control unit 88.

The vehicle control unit 88 is, e.g., a microcomputer composed of a CPU (Central Processing Unit), and a RAM (Random Access Memory) and a ROM (Read Only Memory) as semiconductor memories, etc. The vehicle control unit 88 is electromagnetically connected to the start switch device 1 via, e.g., an in-vehicle LAN (Local Area Network) such as CAN (Controller Area Network) or LIN (Local Interconnect Network).

(Configuration of the Biometric Information Sensor 2)

The biometric information sensor 2 is configured to read, e.g., a fingerprint of the operating finger 9 as the biometric information 23, as shown in FIGS. 1A and 2B. However, the biometric information 23 is not limited to the fingerprint of the operating finger 9 and may be a vein, etc., of the operating finger 9.

In case of reading, e.g., a fingerprint, the biometric information sensor 2 used here is a sensor of optical, capacitive, electric field strength measuring, pressure-sensitive, or thermal type which is configured to read a fingerprint.

Meanwhile, in case of reading, e.g., a vein of the operating finger 9, the biometric information sensor 2 used is a sensor configured to read a vein based on reflection of emitted infrared radiation.

Then, in case of reading, e.g., both a fingerprint and a vein, the biometric information sensor 2 used is a sensor configured to extract a fingerprint and a vein by processing an image captured under visible light.

The biometric information sensor 2 in the present embodiment is a capacitive sensor that detects contact of (touch operation by) the operating finger 9 and reads a fingerprint as the biometric information 23, as an example. The biometric information sensor 2 is configured to read the biometric information 23 from the operation finger 9 which is in contact with the reading surface 20 when an operator performs a touch operation on the operation surface 120 of the operating portion 12.

Alternatively, the reading surface 20 may be arranged under the operation surface 120 without being exposed on the operation surface 120. In addition, the shape of the reading surface 20 is not limited to, e.g., a rectangle and may be a circle or an ellipse.

The biometric information sensor 2 is provided with, e.g., the plural detection electrodes which are arranged in rows and columns in a grid pattern under the reading surface 20. As an example, several ten thousand to several hundred thousand detection electrodes are formed and arranged at intervals of several μm to several tens μm.

The biometric information sensor 2 is configured to scan all detection electrodes by, e.g., repeating a process of reading capacitances of the detection electrodes arranged in one row while changing columns and then subsequently reading capacitances of the detection electrodes arranged in a different row. The scanning cycle is about 100 ms, as an example.

The biometric information sensor 2 outputs, e.g., a captured image 22, which is formed based on plural capacitances read by scanning, to the control unit 6. The captured image 22 is formed based on, e.g., capacitances in one cycle.

In particular, the biometric information sensor 2 generates the captured image 22 by, e.g., classifying the capacitances into capacitances of not less than a predetermined threshold value to be assigned "1" and capacitances of less than the threshold value to be assigned "0" and associating the capacitances with the positions of the detection electrodes.

The captured image 22 shown in FIG. 2B is produced in such a manner that the positions of the detection electrodes assigned "1" described above are shown in black and the positions of the detection electrodes assigned "0" are shown in white, as an example. The circles in the drawing are added to show some of characteristic features 7 (described later).

The high-capacitance positions are positions of ridges of the fingerprint which are close to the detection electrodes, hence, capacitance is high. Meanwhile, the low-capacitance positions are positions of valleys of the fingerprint which are far from the detection electrodes, hence, capacitance is low. Therefore, as an example, the captured image 22 shown in FIG. 2B is obtained when the high-capacitance positions are shown in black and the low-capacitance positions are shown in white. The image shown in black in the captured image 22 is the read biometric information 23.

The control unit 6 may be configured to, e.g., select a captured image 22, which is suitable for extraction of the characteristic features 7, from plural captured images 22 periodically captured after the contact of the operating finger 9 with the reading surface 20.

(Configuration of the Illumination Unit 4)

As an example, the illumination unit 4 is provided with a light guide 40 and first to fifth light sources 41-45, as shown in FIGS. 1A and 1B.

The light guide 40 is e.g., in the form of bezel and is arranged between the main body 10 and the operation surface 120 so as to surround the operation surface 120. The light guide 40 is configured to, e.g., guide light output from the light sources so that a circumference of the operation surface 120 is illuminated. The light guide 40 is formed of, e.g., a resin with high light transmittance such as acrylic and silicon.

As a modification, the start switch device 1 may be configured that, e.g., light is output from a gap between the main body 10 and the operation surface 120 without using the light guide 40.

The first to fourth light sources 41-44 are arranged, e.g., under the light guide 40. Meanwhile, the fifth light source 45 is a light source to illuminate, e.g., letters 121 which are provided on the operation surface 120. The first to fifth light sources 41-45 are, e.g., LED (light emitting diode) elements. The number and type of the light sources are not limited thereto.

The first light source 41 is, e.g., a white LED element. The first light source 41 emits, e.g., white light based on a drive signal $S_1$ output from the control unit 6, as shown in FIG. 1B.

The second light source 42 is, e.g., a blue LED element. The second light source 42 emits, e.g., blue light based on a drive signal $S_2$ output from the control unit 6, as shown in FIG. 1B.

The third light source 43 is, e.g., a green LED element. The third light source 43 emits, e.g., green light based on a drive signal $S_3$ output from the control unit 6, as shown in FIG. 1B.

The fourth light source 44 is, e.g., a red LED element. The fourth light source 44 emits, e.g., red light based on a drive signal $S_4$ output from the control unit 6, as shown in FIG. 1B.

The fifth light source 45 is, e.g., a white LED element. The fifth light source 45 emits, e.g., white light based on a drive signal $S_5$ output from the control unit 6, as shown in FIG. 1B.

(Configuration of the Control Unit 6)

The control unit 6 is, e.g., a microcomputer composed of a CPU performing calculation and processing, etc., of the acquired data according to a stored program, and a RAM and a ROM as semiconductor memories, etc. The ROM stores, e.g., a program for operation of the control unit 6. The RAM is used as, e.g., a storage area for storing registered biometric information 60, an authentication threshold value 61, illumination pattern information 62 and calculation results, etc. In addition, the control unit 6 has, inside thereof, a means for generating a clock signal, and operates based on the clock signal.

The registered biometric information 60 is, e.g., information associating a registered person's name with a template of each registered person. The registered person's name may be associated with, e.g., an electronic key or mobile device, and may be input by operating an input device. However, it is not limited thereto.

The template is created based on the read biometric information 23 and is composed of mainly the characteristic features 7. Here, registering the biometric information 23 means that a temperate is created based on the biometric information 23 and the registered biometric information 60 is produced by associating the created template with the registered person's name Next, the characteristic feature 7 will be described.

The control unit 6 performs, e.g., an extraction process on the captured image 22 and extracts the characteristic features 7. The extraction process is, e.g., a process of extracting fingerprint ridges, etc.

The characteristic feature 7 is, e.g., a center point, a bifurcation point, an ending point or a delta, etc., as shown in FIG. 2B, but it is not limited thereto. The center point is a point at the center of the fingerprint. The bifurcation point is a point at which a fingerprint ridge bifurcates. The ending point is a point at which a ridge ends. The delta is a point at which ridges from three directions meet.

The control unit 6 extracts, e.g., the characteristic features 7 from the captured image 22. The control unit 6 then compares, e.g., the acquired registered biometric information 60 to the biometric information 23 from which the characteristic features 7 are extracted, and calculates a degree of similarity based on the positions of the characteristic features 7 and distances between the characteristic features 7, etc. Then, when the degree of similarity is not less than the authentication threshold value 61, the control unit 6 outputs the instruction signal $S_6$ upon determination that the biometric information 23 is successfully authenticated.

The authentication threshold value 61 is defined as 80% of the number of the characteristic features 7 used for authentication, as an example. In other words, when, e.g., the number of the characteristic features 7 of the biometric information 23 used for authentication is eighty and when not less than sixty-four characteristic features 7 match those of the registered biometric information 60, the control unit 6 determines that the operator is a registered person. The match here includes match of the position of the characteristic feature 7 and a distance between the characteristic features 7, etc.

The biometric authentication is not limited to being performed by the authentication method using the degree of similarity of the characteristic features 7 and may be performed by an authentication method such as pattern matching.

The vehicle control unit 88 may be configured to implement, e.g., settings of on-vehicle devices which have been set by the registered person who is biometrically authenticated based on the acquired instruction signal $S_6$. The on-vehicle device when being, e.g., a seat driving device moves a seat to a seat position which has been set by the registered person. Meanwhile, the on-vehicle device when being, e.g., an air conditioner implements the settings, such as the set temperature and the air volume, which have been set by the registered person. Furthermore, the on-vehicle device when being, e.g., a mirror driving device drives mirrors to the positions which have been set by the registered person. Electromagnetic connection is, e.g., connection using at least one of connection via a conductor, connection via light which is a kind of electromagnetic wave, and connection via radio waves which is also a kind of electromagnetic wave.

The illumination pattern information 62 is information of illumination patterns of the illumination unit 4 for providing feedback about the operation by light performance. The control unit 6 illuminates, e.g., a circumference of the operation surface 120 with an illumination pattern along first to fourth intervals A to D, as shown in FIG. 3. Then, as shown in FIG. 4, the control unit 6 stores at least one of illumination patterns a-e along the first to fourth intervals A to D, as the illumination pattern information 62, as an example. However, the illumination pattern is not limited to the illumination patterns a—e.

The first to fourth intervals A to D are divided based on, e.g., ON/OFF of the brake device 86, touch/no touch on the biometric information sensor 2, completed/in process/not processing as the acquisition status of the captured image 22, and ON/OFF as the start status of the drive system 87, as shown in FIG. 3.

The first interval A is, e.g., an interval from when a door of the vehicle 8 is opened to when the brake device 86 is operated. In particular, the first interval A is, e.g., an interval in which the brake device 86 is OFF, the biometric information sensor 2 is not touched, the acquisition status of the captured image 22 is no processing, and the start status of the drive system 87 is OFF, as shown in FIG. 3. The first interval A shown in FIG. 3 is, e.g., from time to $t_0$ time $t_1$.

The second interval B is, e.g., an interval from when the brake device 86 is operated to when a touch operation performed on the operation surface 120 is detected. In particular, the second interval B is, e.g., an interval in which the brake device 86 is ON, the biometric information sensor 2 is not touched, the acquisition status of the captured image 22 is no processing, and the start status of the drive system 87 is OFF, as shown in FIG. 3. The second interval B shown in FIG. 3 is, e.g., from time $t_1$ to time $t_2$.

The third interval C is, e.g., an interval from when the touch operation is detected to when acquisition of the captured image 22 is completed. In particular, the third interval C is, e.g., an interval in which the brake device 86 is ON, the biometric information sensor 2 is touched, the acquisition status of the captured image 22 is transitioning from no processing to in process, and the start status of the drive system 87 is OFF, as shown in FIG. 3. The third interval C shown in FIG. 3 is, e.g., from time $t_2$ to time $t_4$.

In this regard, in the third interval C, for example, the acquisition status of the captured image 22 is no processing from time $t_2$ to time $t_3$, and then, acquisition of the captured image 22 is started at time $t_3$ and is completed at time $t_4$.

The fourth interval D is, e.g., an interval from when the acquisition of the captured image 22 is completed to when the drive system 87 is started. In particular, the fourth interval D is, e.g., an interval in which the brake device 86 is ON, the biometric information sensor 2 is not touched, the acquisition status of the captured image 22 is completed, and the start status of the drive system 87 is OFF, as shown in FIG. 3. The fourth interval D shown in FIG. 3 is, e.g., from time $t_4$ to time $t_5$.

Since the fourth interval D here is an interval in which the user sees and understands the illumination pattern and then takes his/her finger off the operation surface 120 as an example, change from touch to no touch occurs within this interval. In addition, in the fourth interval D, authentication is performed based on the biometric information 23, which is based on the obtained captured image 22, and the registered biometric information 60.

The control unit 6 has an illumination pattern(s) corresponding to the first to fourth intervals A to D. The illumination patterns a-e shown in FIG. 4 are examples and it is not limited thereto.

As show in FIG. 4, the illumination pattern a is, e.g., an illumination pattern produced by using the same color and switching between blinking and solid light, and it is an illumination pattern configured such that slow blinking white light is provided in the first interval A, rapid blinking white light is provided in the second interval B and the third interval C, and solid white light is provided in the fourth interval D. The illumination pattern a is produced using the first light source 41 in the first to fourth intervals A-D.

As show in FIG. 4, the illumination pattern b is, e.g., one of illumination patterns produced by using solid light and switching colors, and it is an illumination pattern configured such that solid white light is provided in the first to third intervals A-C and solid blue light is provided in the fourth interval D. The illumination pattern b is produced using the first light source 41 in the first to third intervals A-C and the second light source 42 in the fourth interval D.

As show in FIG. 4, the illumination pattern c is, e.g., one of illumination patterns produced by using solid light and switching colors, and is different from the illumination pattern b in that the color is changed according to the result of acquisition of the captured image 22.

The illumination pattern c is an illumination pattern configured such that, e.g., solid white light is provided in the first to third intervals A-C, solid blue light is provided in the fourth interval D-1, and solid red light is provided in the fourth interval D-2. The illumination pattern c is produced using the first light source 41 in the first to third intervals A-C, the second light source 42 in the fourth interval D-1, and the fourth light source 44 in the fourth interval D-2.

In the illumination patterns c-e, the fourth interval D is divided into the fourth interval D-1 and the fourth interval D-2. The fourth interval D-1 is an illumination pattern provided when the captured image 22 is successfully acquired. Meanwhile, the fourth interval D-2 is an illumination pattern provided when failed to acquire the captured image 22.

As shown in FIG. 4, the illumination pattern d is, e.g., one of illumination patterns produced by using solid light and switching colors and is different from the illumination pattern c in that the color is changed after a touch operation is detected.

The illumination pattern d is an illumination pattern configured such that, e.g., solid white light is provided in the first interval A and the second interval B, solid blue light is provided in the third interval C, solid green light is provided in the fourth interval D-1, and solid red light is provided in the fourth interval D-2. The illumination pattern d is produced using the first light source 41 in the first interval A and the second interval B, the second light source 42 in the third interval C, the third light source 43 in the fourth interval D-1, and the fourth light source 44 in the fourth interval D-2.

As shown in FIG. 4, the illumination pattern e is, e.g., an illumination pattern produced by switching between blinking and solid light and also switching colors, and is different from the illumination pattern d in that the blinking cycle is changed after the brake device 86 is operated.

The illumination pattern e is an illumination pattern configured such that, e.g., slow blinking white light is provided in the first interval A, rapid blinking white light is provided in the second interval B, solid blue light is provided in the third interval C, solid green light is provided in the fourth interval D-1, and solid red light is provided in the fourth interval D-2. The illumination pattern e is produced using the first light source 41 and also the fifth light source 45 to illuminate the letters 121 in the first interval A, the first light source 41 in the second interval B, the second light source 42 in the third interval C, the third light source 43 in the fourth interval D-1, and the fourth light source 44 in the fourth interval D-2.

The illumination patterns a-e are illumination patterns in which, e.g., switching between blinking/solid or between colors, etc., is performed between the third interval C and the fourth interval D so that it is easy for the user to find the timing to take the finger off the operation surface 120.

Alternatively, the illumination pattern may be configured to be a pattern in which, e.g., high and low intensity of light is included or switching of colors is periodically performed within interval.

Figure 5:
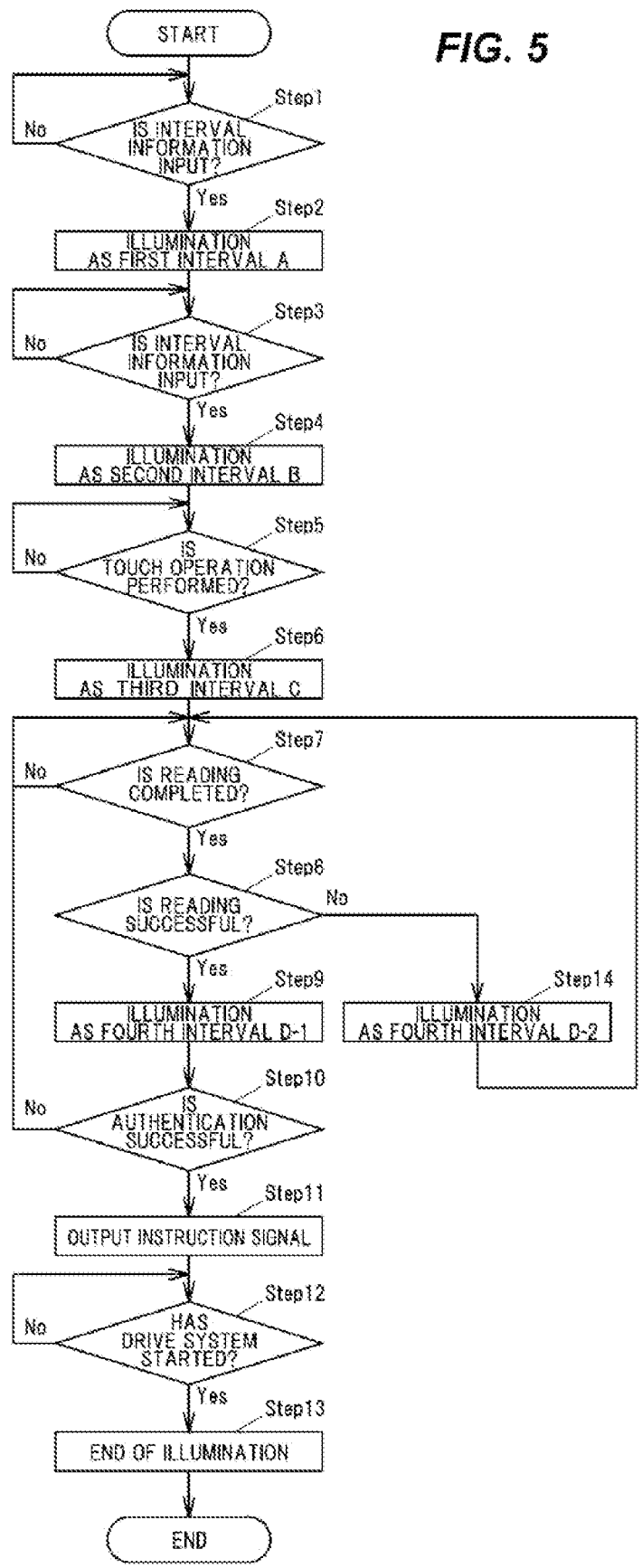
FIG. 5 is a flowchart showing an operation of the start switch device in the embodiment.

Next, an operation of the start switch device 1 in the present embodiment will be described along with the flowchart of FIG. 5. In the following description, an example in which the illumination pattern is the illumination pattern e will be explained.

(Operation)

When, e.g., a user carrying an electronic key comes close to the vehicle 8 and is successfully authenticated, the vehicle control unit 88 unlocks the doors of the vehicle 8. Then, when the user opens the door, the vehicle control unit 88 outputs the interval information $S_7$.

When received the interval information $S_7$, i.e., when it is "Yes" in Step 1 (Step 1: Yes), the control unit 6 of the start switch device 1 determines the corresponding interval and performs illumination based on the illumination pattern information 62. Since the interval information $S_7$ indicates that the door is opened, the control unit 6 outputs the drive signal $S_1$ to the first light source 41 and the drive signal $S_5$ to the fifth light source 45 based on the illumination pattern information 62 to perform illumination as the first interval A (Step 2).

When the operation signal $S_8$ is input from the brake device 86, the vehicle control unit 88 outputs the interval information $S_7$ upon determination that the brake device 86 is operated.

Next, when it is "Yes" in Step 3, i.e., when the interval information $S_7$ indicating that the brake device 86 is turned ON is input (Step 3: Yes), the control unit 6 determines the corresponding interval and performs illumination based on the illumination pattern information 62. Since the interval information $S_7$ indicates that brake device 86 is turned ON, the control unit 6 outputs the drive signal $S_1$ for blinking in a faster cycle than the first interval A to the first light source 41 based on the illumination pattern information 62 to perform illumination as the second interval B (Step 4).

Next, based on the captured image 22 from the biometric information sensor 2, the control unit 6 determines whether or not a touch operation is performed. When it is "Yes" in Step 5, i.e., when it is determined that a touch operation is performed (Step 5: Yes), the control unit 6 outputs the drive signal $S_2$ to the second light source 42 based on the illumination pattern information 62 to perform illumination as the third interval C (Step 6).

Next, the control unit 6 acquires the captured image 22 to be used for authentication. When it is "Yes" in Step 7, i.e., when reading is completed (Step 7: Yes) and reading is successful (Step 8: Yes), the control unit 6 outputs the drive signal $S_3$ to the third light source 43 based on the illumination pattern information 62 to perform illumination as the fourth interval D indicating successful reading (Step 9).

Next, the control unit 6 performs authentication based on the biometric information 23, which is based on the successfully obtained captured image 22, and the registered biometric information 60. When the authentication is successful (Step 10: Yes), the control unit 6 outputs the instruction signal $S_6$ which indicates successful authentication (Step 11).

When the instruction signal $S_6$ indicating successful authentication is input, the vehicle control unit 88 outputs the drive instruction signal $S_9$ to start the drive system 87 and also outputs the interval information $S_7$ indicating that it has been started.

Next, when it is "Yes" in Step 12, i.e., when the interval information $S_7$ indicating that the drive system 87 has been started is input from the vehicle control unit 88, the control unit 6 determines that the drive system 87 has been started (Step 12: Yes) and ends illumination of the fourth interval D (Step 13).

Meanwhile, when the reading failed in Step 8 (Step 8: No), the control unit 6 outputs the drive signal $S_4$ to the fourth light source 44 based on the illumination pattern information 62 to perform illumination as the fourth interval D-2 indicating that the reading failed (Step 14), proceeds the process to Step 7, and performs reading again. In this regard, when the status changes from touch to no touch in Step 7 which is carried out to perform reading again, the control unit 6 ends illumination.

Then, when the authentication is not successful in Step 10 (Step 10: No), the control unit 6 proceeds the process to Step 7, and performs reading again. In this regard, when the status changes from touch to no touch in Step 7 which is carried out to perform reading again, the control unit 6 ends illumination.

Effects of the Embodiment

The start switch device 1 in the present embodiment can reduce operational burden of users. In particular, the start switch device 1 provides feedback about the operation using light performance Therefore, unlike when such a configuration is not adopted, the user can easily know that the touch operation is detected or reading of biometric information is completed. In addition, since timing to take the finger off is clear before the start of the drive system 87 due to the feedback about the operation using light performance, it is not necessary to hold the touch operation until the start-up and the start switch device 1 thereby can reduce operational burden of users.

With the start switch device 1, change from one interval to another is clear since blinking, solid light, cycle, color, etc., of the illumination are changed from the third interval C to the fourth interval D. Therefore, it is easier for users to find the timing to take the finger off, as compared to when such a configuration is not adopted.

The start switch device 1 can illuminate differently depending on whether or not reading of the captured image 22 is successful. Therefore, as compared to when such a configuration is not adopted, it is easy for users to know why the drive system 87 does not start and a feeling of distrust in authentication is thereby reduced.

As another embodiment, a biometric information authenticating system provided with the start switch device 1 and the vehicle control unit 88 may be constructed.

The biometric information authenticating system has a start switch device having a biometric information sensor to detect contact of an operating finger with a reading surface and to read biometric information of the operating finger, an illumination unit having at least one light source, and a control unit to control the illumination unit by an illumination pattern including a combination of turning on and off of the at least one light source based on vehicle information indicating the state of the vehicle and input thereto, and a vehicle control unit to output the vehicle information to the control unit.

This vehicle information is, e.g., the interval information $S_7$ described above. The biometric information authenticating system determines an interval based on, e.g., operation status of the brake device 86 indicated by the interval information $S_7$, a result of detecting touch or no touch on the biometric information sensor 2, acquisition status of the captured image 22, and start status of drive system 87 indicated by the interval information $S_7$, and performs illumination corresponding to the determined interval.

Although some embodiments and modifications of the invention have been described, these embodiments and modifications are merely examples and the invention according to claims is not to be limited thereto. These new embodiments and modifications may be implemented in various other forms, and various omissions, substitutions and changes, etc., can be made without departing from the gist of the invention. In addition, all combinations of the features described in these embodiments and modifications are not necessary to solve the problem of the invention. Further, these embodiments and modifications are included within the scope and gist of the invention and also within the invention described in the claims and the range of equivalency.

REFERENCE SIGNS LIST

1 STRAT SWITCH DEVICE
2 BIOMETRIC INFORMATION SENSOR
4 ILLUMINATION UNIT
6 CONTROL UNIT
8 VEHICLE
9 OPERATING FINGER
10 MAIN BODY
12 OPERATING PORTION
20 READING SURFACE
23 BIOMETRIC INFORMATION
40 LIGHT GUIDE
41-45 FIRST TO FIFTH LIGHT SOURCES
62 ILLUMINATION PATTERN INFORMATION
87 DRIVE SYSTEM
88 VEHICLE CONTROL UNIT

The invention claimed is:

1. A biometric information authenticating device, comprising:
    a vehicle start switch device comprising a biometric information sensor to detect contact of an operating finger of an operator with a fingertip reading surface and to read biometric information of the operating finger;
    an illumination unit comprising at least one light source; and
    a control unit to indicate completion and successful reading of the biometric information by an illumination pattern including a combination of turning on and off of the at least one light source to allow the vehicle operator to remove the operating finger from contact with the reading surface before start-up of the vehicle from the switch device.

2. The biometric information authenticating device according to claim 1, wherein the biometric information sensor reads one of or both of a fingerprint pattern and a vein pattern as the biometric information.

3. The biometric information authenticating device according to claim 1, wherein, when contact of the operating finger with the reading surface is detected, the control unit controls the illumination unit to produce a different illumination pattern from the illumination pattern produced at the time of completion of reading of the biometric information.

4. The biometric information authenticating device according to claim 3, wherein the control unit makes a difference between the illumination pattern produced at the time of detection of the operating finger with the reading surface and the illumination pattern produced at the time of completion of reading of the biometric information by switching between blinking and solid light in the same color.

5. The biometric information authenticating device according to claim 1, wherein the control unit controls the illumination unit to change the illumination pattern when reading of the biometric information is successful and when failed.

6. The biometric information authenticating device according to claim 1, wherein, upon successful authentication of the biometric information that is read during contact of the operating finger, the control unit outputs a signal to permit a drive system of a vehicle to start.

7. The biometric information authenticating device according to claim 1, wherein
the reading surface of the biometric information sensor is arranged so as to be able to read the biometric information of the operating finger in contact with an operation surface of an operating portion of the vehicle start switch device, and
the illumination unit outputs a circle of light that surrounds the operation surface.

8. The biometric information authenticating device according to claim 7, wherein the illumination unit comprises a light guide that is arranged between the operation surface and a main body positioned around the operating portion and surrounds the operation surface, and light output from the at least one light source is guided by the light guide.

9. The biometric information authenticating device according to claim 7, wherein the illumination unit is configured that light output from the at least one light source is output from a gap formed between the operation surface and the main body positioned around the operating portion.

10. A biometric information authenticating system, comprising:
a start switch device comprising a biometric information sensor to detect contact of an operating finger with a reading surface and to read biometric information of the operating finger,
an illumination unit comprising at least one light source, and a control unit to control the illumination unit by an illumination pattern including a combination of turning on and off of the at least one light source; and
a vehicle control unit electromagnetically connected to the start switch device and each unit of a vehicle,
wherein the vehicle control unit determines the state of the vehicle and outputs vehicle information to the control unit based on a detection result of contact of the operating finger with the reading surface, completion and successful reading of the biometric information, operation status of the vehicle, and start status of a drive system, and the control unit controls the illumination unit to produce the illumination pattern corresponding to the vehicle information, and
wherein the reading surface of the biometric information sensor is arranged so as to be able to read the biometric information of the operating finger in contact with an operation surface of an operating portion, and
wherein the illumination unit outputs a circle of light that surrounds the operation surface.

* * * * *